United States Patent [19]

Zimmermann et al.

[11] Patent Number: 5,427,934
[45] Date of Patent: Jun. 27, 1995

[54] GENETIC ENGINEERING PROCESS FOR THE PRODUCTION OF S-(+)-2,2-DIMETHYLCYCLOPROPANECARBOXAMIDE BY MICROORGANISMS

[75] Inventors: Thomas Zimmermann, Naters; Karen Robins, Visp; Olwen M. Birch; Elisabeth Böhlen, both of Naters, all of Switzerland

[73] Assignee: Lonza Ltd., Gampel/Valais, Switzerland

[21] Appl. No.: 918,023

[22] Filed: Jul. 24, 1992

[30] Foreign Application Priority Data

Jul. 26, 1991 [CH] Switzerland .......................... 2247/91

[51] Int. Cl.$^6$ .................. C12P 13/02; C12N 9/14; C12N 15/00
[52] U.S. Cl. .................................. 435/129; 435/195; 435/320.1; 435/252.33; 435/252.3; 536/23.2
[58] Field of Search ................. 435/69.1, 129, 849, 435/874, 878, 252.33, 252.2, 252.3, 195, 320.1; 536/23.2, 23.7

[56] References Cited

U.S. PATENT DOCUMENTS

| | | | |
|---|---|---|---|
| 2,511,867 | 7/1948 | Neuberg et al. | 195/29 |
| 3,897,308 | 7/1975 | Li et al. | 195/63 |
| 5,149,869 | 9/1992 | Meul et al. | 562/506 |
| 5,273,903 | 12/1993 | Robins et al. | 435/280 |

FOREIGN PATENT DOCUMENTS

| | | |
|---|---|---|
| 048301 | 3/1982 | European Pat. Off. |
| 0264457 | 4/1988 | European Pat. Off. |
| 0416282 | 3/1991 | European Pat. Off. |
| 0433117 | 6/1991 | European Pat. Off. |
| 0502525 | 9/1992 | European Pat. Off. |

OTHER PUBLICATIONS

Stanier et al. J. Gen. Microbiol. (1966), 43, 159–271.
Zeyer, J., et al., Applied and Environmental Microbiology, vol. 50, No. 6, pp. 1409–1413, Dec., 1985.
Stryer, L. Biochemistry. 1981. pp. 104 & 160.
Chesney, R. H., et al., J. Mol. Biol., 130, (1979), pp. 161–173.
Fiedler, S., et al., Analyt. Biochem., 170, (1988), pp. 38–44.
Mol. Gen. Genet., 192, (1983), pp. 293 and 294.
Boyer, H. W., et al., J. Mol. Biol., 41, (1969), pp. 459–472.
Kulla et al., Arch. Microbiol., 135, (1983), pp. 1–7.
Hochstrasser et al., Applied And Theoretical Electrophoresis, 1, (1988), pp. 73–76.
Current Protocols of Molecular Biology, John Wiley & Sons, New York, (1988), Section 2.
Current Protocols of Molecular Biology, John Wiley & Sons, New York, (1987), Section 2.9ff.
Schweizer, H., et al., Mol Gen. Genet., 192, (1983), pp. 293–294.
Current Protocols In Molecular Biology, John Wiley & Sons, New York, (1987), Section 2.
Chemical Abstracts, vol. 103, No. 15, (Oct. 14, 1985) 123058c.
Chemical Abstracts, vol. 95, No. 19, (Nov. 9, 1981), 167131s.

Primary Examiner—Robert A. Wax
Assistant Examiner—Keith D. Hendricks
Attorney, Agent, or Firm—Fisher, Christen & Sabol

[57] ABSTRACT

A genetic engineering process for the production of S-(+)-2,2-dimethylcyclopropanecarboxamide. For this purpose, a new DNA is isolated from a microorganism that codes for a stereospecific hydrolase. This DNA is then ligated in an expression vector, and a hybrid plasmid results, which is transformed into microorganisms. These microorganisms are then able to biotransform the R-(−) isomer in racemic R,S-(±)-2,2-dimethylcyclopropanecarboxamide into R-(−)-2,2-dimethylcyclopropanecarboxylic acid, and optionally active S-(+)-2,2-dimethylcyclopropanecarboxamide is obtained.

20 Claims, 5 Drawing Sheets

FIG. 3a

Pvu II

```
           c   agc tgc ggt tgc agg cca gcc agc gcc ttc gca agg cgt tcg gct gca
gct gct cca gcg tga ccg agg cgg atg ggt cgc atg ggt tct ccg gag cct ttc ccc gct ttc cct gcc gtg
cgc ccc gca gcc tgc tgg ccg cct gag caa cgc tga ggt cac gcc cgg gcg gcg cgg cct cct ccc gtg
cgt ccc gtg cgg ctt ttc cag tgc aac aac ggt gcc ccg gag ccg ggc aga cat gcc ATG AAT AGC GAA CTG CAC CAT
                                                                              MET Asn Ser Glu Leu His His
CTC GAA CTG GAG GTG GGG CGC GAG ATC CAG CGC ATT TCG TCG GAA GAG GTG ACC CGC CAC ATG GAC CTG GCG CGC ATC GAG GCC
Leu Glu Leu Glu Val Gly Arg Glu Ile Gln Arg Ile Ser Ser Glu Glu Val Thr Arg His MET Asp Leu Ala Arg Ile Glu Ala
GTG GAC GCG CGG CTG CAC AGC AGC TAC GTG ACG GTG CAG CAG ATG GCC GAC GCC GAG ATC GCG GAG GCG CAG GGC
Val Asp Ala Arg Leu His Ser Ser Tyr Val Thr Val Gln Gln MET Ala Asp Ala Glu Ile Ala Glu Ala Gln Gly
       Kspl                                           Smal
GCC GCC GCG GTG CGC ACG TGC CGT GGC GCT CAA GGA CCT GTG GCT GCC CAC CAC GCA AAT GAC GCT GCA
Ala Ala Ala Val Arg Thr Cys Arg Gly Ala Gln Gly Pro Val Ala Ala His His Ala Asn Asp Ala Ala
                                                                                    Pstl
CCG CGA CCA TCG CCC CAC GGA AGA TGC CAC CGT GGT GCG CAG CGC CCT CAT CCT GGG GCC CGG CAA CTC GTC CAG GAC CGA
Pro Arg Pro Ser Pro His Gly Arg Cys His Arg Gly Ala Gln Arg Pro His Pro Gly Ala Arg Leu Val Gln Asp Arg
AGG CGC CTT CGC CGA CCA CCA TCC CGA GAT CAC CCC CGT CAA GCT CCT ATG GCC CGG CCA GCT ATG GCC CTT CCG CAA CGG CAT
Arg Arg Leu Arg Arg Pro Pro Ser Arg Asp His Pro Arg Gln Ala Pro MET Ala Arg Pro Ala MET Ala Leu Pro Gln Arg His
                                                                              Smal
GGG CGT GGC CAC GGC GGC GGG GCT GTG GCT GGG CAG CAC CGG GGC GGG CTC CAT CCG CTC TCC ATC GGC CGG CAA CGG CAT
Gly Arg Gly His Gly Gly Gly Ala Val Ala Gly Gln His Arg Gly Gly Leu His Pro Leu Ser Ile Gly Arg Gln Arg His
CAC GGG GCT CAA GCC CAC CTG GGG GCT CTT CGA ACT CGC CGC CGG CCA CAT AGG CCC GAT GGC GCG
His Gly Ala Gln Ala His Leu Gly Gly Leu Arg Thr Arg Arg Arg Pro His Arg Pro Asp Gly Ala
```

FIG. 3b

```
CAG TGC TGC CGA AGC CAT GCT CGC GGC CAT CGC GGC GGA CCC GCT GGA CCC TAC GGC CAG GTG CCA CCA GTG CAG CGT GCC CGA CTA
Gln Cys Cys Arg Ser His Ala Arg Gly His Arg Gly Gly Pro Ala Gly Pro Tyr Gly Gln Val Pro Pro Val Gln Arg Ala Arg Leu

TCT GGC CAT GAT GAC GCG CGG ATT CTC CGG GCT GCG CCT CGG CAT CCA CCG GCA ATG GGC GCA CTG GGA CGG TGC GGA TGC CCC CCA
Ser Gly His Asp Asp Ala Arg Ile Leu Arg Ala Ala Pro Arg His Pro Pro Ala MET Gly Ala Leu Gly Arg Cys Gly Cys Pro Pro

GGC GGT GGA GCA GGC CCT GGC GGT GGT GGC GGT GGC GCA GCC CTG GGG GGC GGA CGT GCA GGA CGT GGA TGC CAC GGC GGT GGA GGA
Gly Gly Gly Ala Gly Pro Gly Gly Gly Gly Gly Gly Ala Ala Leu Gly Gly Gly Arg Ala Gly Arg Gly Cys His Gly Gly Gly Gly

CTG GCC GGC GCT GTG CGC GGT GGA GAC CGC GTC GCG CGG GCT GCA GCG CCT CCG CTT TCC CGA TGC CGA TGG CCA CCC CGG GCT CGC CGG
Leu Ala Gly Ala Val Arg Gly Gly Asp Arg Val Ala Arg Gly Ala Ala Pro Arg Leu Ser Arg Cys Arg Trp Pro Pro Arg Ala Arg Arg
                                                                                  Stul            Smal GTT GAT CGA CCT GGT GGG GCT GCT GTC CTG CAC CAC CGA CGG CGG GCG GAC CTT CAC GCG CGC CTT GGG GCC CGG GGT GCG TGC ACT
Val Asp Arg Pro Gly Gly Ala Ala Val Leu His His Arg Arg Arg Ala Ala Leu His His Ala Ala Gly Pro Arg Gly Ala Cys Thr CTT CGC GGC GCA GGT GGA TCT GCT GCT GGT CCC CGA CAC CTG GGC CTT TGC CCC GGT CCG CTT CAC GGG CCG GGT GGC CTC CGA CGA
Leu Arg Ala Ala Gly Gly Ser Ala Ala Gly Pro Arg His Leu Gly Leu Cys Pro Val Arg Phe Thr Gly Arg Gly Gly Leu Arg Arg GCT GTT CTC GGG CAT GCT GCG CTA CAC CAC CTG CCC GTT CGA CCT CAC GGG CCG CAG CCC GCA ACG CAT GAT CAC GCT GCC CGG ACG CAC TTC TGA ggg
Ala Val Leu Gly His Ala Ala Leu His His Leu Pro Val Arg Pro His Gly Pro Gln Pro Ala Thr His Asp His Ala Ala Arg Thr His Phe --- cgc gcc cgt ggc ctt cca gtt cgt ggc ccc cga ctt ggc cct gct ggt gcg ggg cgc gct gcg gtt cca gca ggc cac gga ctg gca cag gca aca ccc gca gca tgc tgc ctg agc cgc ctg cag ggg cag gcc ggt gcg aca cgg gcg gcc tgt cac ttc cta gac gat gtc ctt gat cga gat gga agg tgt cgc caa gtc ctg ggg ctg ggc gca ggc gct gca ggc gga tct gcg cat tga acc cgg atc
                                                                                              BamHl
c
```

FIG. 4

DNA-oligomer (mixture)

```
                T      T    TCT    A    T T      T
5'     ATG    AAC    GAC    AGC   GAG   CTC    CAC    CA    3'
                            C            C
                            A            A

AS     Met    Asn    Asp    Ser   Glu   Leu    His         AS
```

FIG. 5

DNA-"Antisense" oligomer (mixture)

```
              A      C     T      T      T      T
5'     TG    GAT    TTC   CCG    CCC    CAC    CTC    3'
                          G      G      G
                                 A      A

AS           Ile    Glu   Arg    Gly    Val    Glu    AS
```

GENETIC ENGINEERING PROCESS FOR THE PRODUCTION OF S-(+)-2,2-DIMETHYLCYCLOPROPANECARBOX-AMIDE BY MICROORGANISMS

BACKGROUND OF THE INVENTION

1. Field Of The Invention

The invention relates to a new process for the production of S-(+)-2,2-dimethylcyclopropanecarboxamide with new microorganisms suitable for the process. These microorganisms have been transformed with a new gene, which produces a stereospecific hydrolase, and thus is capable of biotransforming the R-(−)-isomer in racemic R,S-(±)-2,2-dimethylcyclopropanecarboxamide into the corresponding acid, and optically active S-(+)-2,2-dimethylcyclopropanecarboxamide results.

2. Background Art

Hereinafter, 2,2-dimethylcyclopropanecarboxamide may be abbreviated 2,2-DMCPCA and 2,2-dimethylcyclopropanecarboxylic acid may be abbreviated 2,2-DMCPCS.

Optically pure S-(+)-2,2-DMCPCA is used as the initial material for the production of the dehydropeptidase inhibitor cilastatin, which is administered in therapy together with penem or carbapenem antibiotics, to prevent inactivation of the antibiotics by a renal dehydropeptidase in the kidneys (see European Published Patent Application No. 048301).

Examples of microorganisms which produce a stereospecific hydrolase for the R-(−)-2,2-DMCPCA are microorganisms of the species *Comamonas acidovorans* A:18 (DSM No. 6315), *Bacterium sp.* VIII:II (DSM No. 6316), *Pseudomonas sp.* NSAK:42 (DSM No. 6433) and *Comamonas acidovorans* TG 308 (DSM No. 6552) as well as their descendants and mutants. These microorganisms have already been described in detail in European Published Patent Application No. 92103780.0 (and in copending U.S. Ser. No. 845,034, filed on Mar. 3, 1992).

BROAD DESCRIPTION OF THE INVENTION

The main object of the invention is to provide new microorganisms as production strains by recombinant DNA techniques, in which the catalytic ability as well as the expression of this hydrolase gene can be considerably increased relative to the known process. According to the invention the object of the invention is achieved with a new DNA, which codes for the hydrolase gene, with new hybrid plasmids containing this DNA, with new microorganisms which have been transformed with this hybrid plasmid, and with the new process of the invention. Other objects and advantages of the invention are set out herein or are obvious herefrom to one skilled in the art.

The objects and advantages of the invention are achieved by the processes, the DNA, the DNA fragments, the hybrid plasmids and the microorganisms of the invention.

The invention involves a genetic engineering process for the production of S-(+)-2,2-dimethylcyclopropanecarboxamide. R-(−)-2,2-dimethylcyclopropanecarboxamide in racemic R,S-(+)-2,2-dimethylcyclopropanecarboxyamide, is biotransformed by means of microorganisms which are transformed with a gene that produces a stereospecific hydrolase into R-(−)-2,2-dimethylcyclopropanecarboxylic acid, and optically active S-(+)-2,2-dimethylcyclopropanecarboxamide is obtained, and the latter is isolated.

Preferably the biotransformation is performed with microorganisms which have been transformed with a gene which is characterized by the restriction map which is represented in FIG. 1. Preferably the biotransformation is performed with microorganisms, which have been transformed with a DNA fragment (SEQ ID NO: 1), which codes for a polypeptide with stereospecific hydrolase activity whose amino acid sequence (SEQ ID NO: 2) is represented in FIG. 3. Preferably the biotransformation is performed with microorganisms, which have been transformed with a DNA fragment (SEQ ID NO: 1), which hybridizes with the DNA fragment which is represented in FIG. 3 and which codes for a polypeptide with stereospecific hydrolase activity. Preferably the biotransformation is performed with microorganisms of genus Escherichia, Pseudomonas, Comamonas, Acinetobacter, Rhizobium or Agrobacterium. Preferably the biotransformation is performed with microorganisms of the species *Escherichia coli*. Preferably the biotransformation is performed with microorganisms of the species *Escherichia coli* XL1-Blue (DSM No. 6551), which have been transformed with the hybrid plasmid pCAR6, or with their descendants and mutants. Preferably the biotransformation is performed with microorganisms of the species *Escherichia coli* DH5 (DSM No. 7053), which have been transformed with the hybrid plasmid pCAR6, or with their descendants and mutants. Preferably the biotransformation is performed with an immobilized stereospecific hydrolase. Preferably the biotransformation is performed in a medium containing racemic R,S-(±)-2,2-dimethylcyclopropanecarboxamide in an amount of 0.2 to 5 percent by weight. Preferably the biotransformation is performed at a pH of 6 to 11 and a temperature of 15° to 55° C.

The invention involves a DNA coding for a stereospecific hydrolase characterized by the restriction mad which is represented in FIG. 1. The invention also involves a DNA fragment (SEQ ID NO: 1) coding for a polypeptide with stereospecific hydrolase activity whose amino acid sequence (SEQ ID NO: 2) is represented in FIG. 3. The invention further involves a DNA fragment that hybridizes with the DNA fragment (SEQ ID NO: 1) which is represented in FIG. 3 and codes for a polypeptide with stereospecific hydrolase activity. Preferably the DNA or the DNA fragment according to any of the above in hybrid plasmid DCAR6, is deposited in *Escherichia coli* XL1-Blue (DSM No. 6551). Preferably any of the above DNA or DNA fragments in hybrid plasmid pCAR6, is deposited in *Escherichia coli* DH5 (DSM No. 7053).

The invention involves a hybrid plasmid composed of an expression vector with any of the above DNA or DNA fragments inserted in it. Preferably the hybrid plasmid is hybrid plasmid pCAR6 composed of any of the above DNA or DNA fragments and expression vector pBLUESCRIPT-KS+, deposited in *Escherichia coli* XL1-Blue (DSM No. 6551). Preferably the hybrid plasmid is hybrid plasmid pCAR6 composed of any of the above DNA or DNA fragments and expression vector pBLUESCRIPT-KS+, deposited in *Escherichia coli* DH5 (DSM No. 7053).

The invention involves microorganisms that have been transformed with any of the above hybrid plasmids. Preferably the microorganisms are of the species *Escherichia coli* XL1-Blue (DSM No. 6551) that have been transformed with hybrid plasmid pCAR6 as well as their descendants and mutants. Preferably the microorganisms are of the species *Escherichia coli* DH5 (DSM No. 7053) that have been transformed with hybrid plasmid pCAR6 as well as their descendants and mutants.

BRIEF DESCRIPTION OF THE INVENTION

In the drawings:

FIG. 3 shows both the amino-acid sequence (SEQ ID NO: 2) and the DNA sequence (SEQ ID NO: 1) of the gene, which codes for the stereospecific hydrolase;

FIG. 4 shows the DNA-oligomer mixture based on the N-terminal peptide sequence of the hydrolase; and FIG. 5 shows the DNA-"antisense" oligomer mixture based on the N-terminal peptide sequence of the hydrolase.

DETAILED DESCRIPTION OF THE INVENTION

Figure 1:
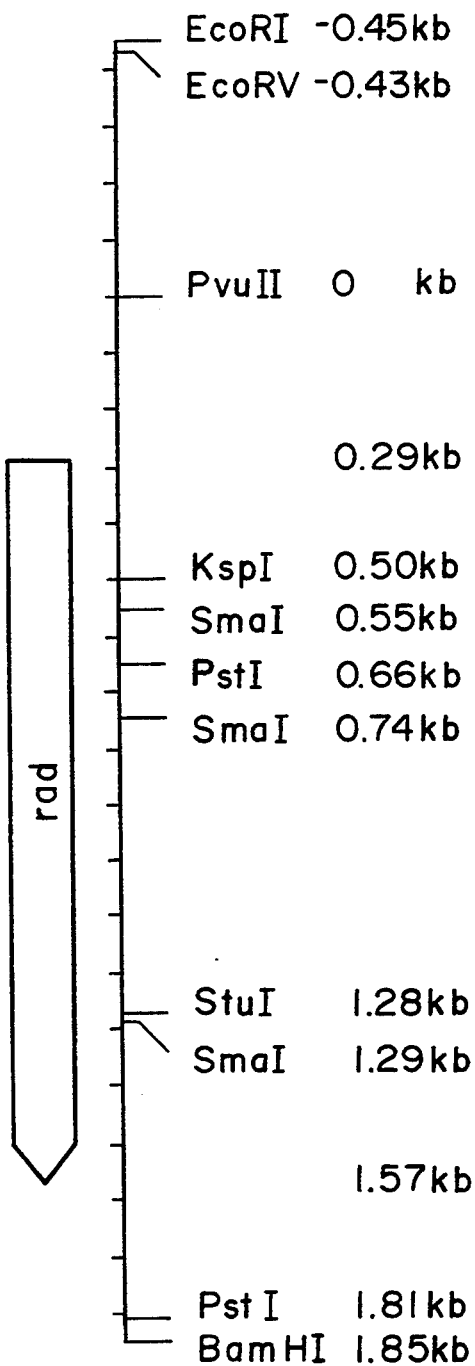
FIG. 1 is the restriction map of the gene.

According to the invention, the process is performed so that R-(−)-2,2-DMCPCA in racemic R,S-(±)-2,2-DMCPCA is biotransformed by microorganisms which are transformed with a gene that produces a stereospecific hydrolase, into R-(−)-2 2-DMCPCs, and optically active S-(+)-2,2-DMCPCA results, and the latter is isolated.

Production of the Transformed Microorganisms

The production of the microorganisms according to the invention, which produces a stereospecific hydrolase, takes place such that:

(A) a DNA coding for hydrolase according to the invention is isolated;

(B) this specific gene sequence is introduced in an expression vector to produce a hybrid plasmid, it possibly being advantageous, where appropriate, to carry out in the hybrid plasmid further modifications which make more effective expression possible.

(C) this hybrid plasmid is introduced by transformation [transformation (E)] into a (D) microorganism (host strain) suitable for the process and this transformed microorganism then (F) forms the producer strain for the process according to the invention [biotransformation (G)].

(A) Isolation of Stereospecific Hydrolase DNA

As a source of the hydrolase DNA, which is designated below as hydrolase DNA (rad) or hydrolase gene (rad), for example, the chromosomal DNA of microorganisms *Comamonas acidovorans* A:18 (DSM No. 6315) or *Comamonas acidovorans* TG 308 (DSM No. 6552), which have already been described in European Published Patent Application No. 92103780.0 and in co-pending U.S. Ser. No. 845,034, can be used. Preferably *Comamonas acidovorans* A:18 is used as the source. The hydrolase DNA can be isolated from a linear gene bank of *Comamonas acidovorans* A:18 in *Escherichia coli* (*E. Coli*) XL1-Blue ® with BLUESCRIPT ® (BLUESCRIPT-KS+ or BLUESCRIPT-SK+) (available from the Stratagene Co., supplier Genofit SA, Geneva, Switzerland) as a commercially available gene bank vector.

For this purpose, for example, first the chromosomal DNA of *Comamonas acidovorans* A:18 is isolated by a modification of the method of R. H. Chesney et al. [J. Mol. Biol., 130, (1979), pages 161 to 173]. This DNA can then be restriction by the conventional molecular biological methods with the restriction enzyme EcoRI and then inserted in the expression vector DNA pBLUESCRIPT-KS+ ® which has previously been restricted in the same way. Then this ligated DNA (hybrid plasmid mixture) can be transformed, for example, according to the method of S. Fiedler and R. Wirth [Analyt. Biochem., 170, (1988), pages 38 to 44], in the competent commercially available microorganisms *E. coli* XL1-Blue ®.

The screening of the gene bank can also take place according to methods known in the art. This entails the hybrid plasmid clones expediently being examined for their ability to grow in a suitable medium with R,S-(±)-2,2-DMCPCA as the sole N-source, a conventional C-source, a suitable inducer and a suitable antibiotic. This screening is then expediently used to select the hybrid plasmid clones which contain the active hydrolase gene (rad) on the hybrid plasmid DNA and, thus, are able to utilize preferentially the R-(−)-2,2-DMCPCA as the sole N-source. These hybrid plasmid clones are then able to hydrolyze the R-(−)-2,2-DMCPCA to the corresponding acid.

The localization of the hydrolase gene (rad) is then expediently carried out in the hybrid plasmid pCAR1 (selected from the hybrid plasmid clones), which consists of the expression vector pBLUESCRIPT-KS+ ® and an EcoRI-"insert" of about 23 kb.

The actual localization of the hydrolase gene (rad) is then expediently carried out using the "Southern-Blot" hybridization known in the art [Current Protocols in Molecular Biology, John Wiley and Sons, New York, (1987), section 2.9]. This expediently entails hybrid plasmid pCAR1 being initially digested with the restriction enzymes BamHI, PstI, PvuII and EcoRI. The DNA fragments resulting from this are then expediently hybridized with radioactively labeled DNA oligomers, which correspond to the N-terminal protein sequences of the hydrolase. In this way an EcoRI-BamHI DNA section which is 2.3 kb in size or a PvuII-BamHI DNA section which is 1.85 kb in size can be labeled on the hybrid plasmid pCAR1.

The DNA oligomers for the hybridization can be obtained according to methods usual to one skilled in the art, for example, by chromotographic concentration of the stereospecific hydrolase, determination of N-terminal amino acid and then synthesize and radioactive labeling of the corresponding DNA sequence.

The now known DNA section, which codes for the stereospecific hydrolase (rad) and whose restriction map is represented (set out) in FIG. 1, is also a part of the invention and can then be isolated with the restriction enzymes BamHI and EcoRI or BamHI and PvuII from the hybrid plasmid pCAR1 according to methods customary in the art, i.e., to determine the complete amino acid sequence via the generic code after analysis of the nucleotide sequence, and to prepare the transformed microorganisms suitable for the process.

Therefore, a component of the invention is also both a DNA fragment (SEQ ID NO: 1), which codes for a polypeptide with stereospecific hydrolase activity, whose amino acid sequence (SEQ ID NO: 2) is represented in FIG. 3, and a DNA fragment, which hybridizes with the DNA fragment (SEQ ID NO: 1) represented in FIG. 3 and codes for this polypeptide.

(B) Ligation of the Specific Gene Sequence (Hydrolase Gene; rad) in Expression Vectors The thus-obtained gene sequence can be ligated by means of conventional techniques of molecular biological techniques with an expression vector DNA, which has previously been restricted in the same way, to give a hybrid plasmid.

Expression vectors usually contain a suitable, in most cases adjustable, promoter (expression control sequence). It is beneficial for one or more unique cleaving sites for the restriction enzymes to be located behind this promoter in the direction of transcription. The required gene section whose expression is of interest is normally then inserted into these cleavage sites.

For the process according to the invention either the expression vectors with a broad host spectrum (broad host range) or, for example, the commercially available expression vector pBLUESCRIPT-KS+ ® can be used. Preferably pBLUESCRIPT-KS+ ® with promoter $P_{Lac}$ (lactose promoter) can be used as the expression vector. It is expedient to restrict expression vector pBLUESCRIPT-KS+ ® with the restriction enzymes EcoRI and BamHI or with PvuII and BamHI, and to ligate the resulting restriction ends with the isolated DNA sequence section (EcoRI-BamHI or PvuII-BamHI), which codes for the stereospecific hydrolase, for example, by T4-DNA-ligase.

(C) Hybrid Plasmids

The invention further relates to the thus-developed hybrid plasmids, which contain the stereospecific hydrolase gene sequence (rad).

Basically all hybrid plasmids, which are able to replicate and express the DNA sequence coding for the hydrolase according to the invention in the selected microorganism (production strain), are suitable. Suitable hybrid plasmids contain from their original expression vector an intact replicon and a marking gene which makes possible the selection and identification of the microorganisms transformed with the hybrid plasmid because of a phenotypic feature. A suitable marker gene confers on the microorganisms, for example resistance to antibiotics.

To achieve an efficient expression in a hybrid plasmid, it is expedient for the hydrolase gene (rad) to be placed correctly in "phase" with the promoter.

Examples of such hybrid plasmids that are suitable for the expression of the hydrolase gene in an *E. coli* strain are the hybrid plasmids pCAR5 and pCAR6, with the marker gene bla (which provides resistance to ampicillin; Ap ®) and to the promoter $P_{Lac}$. Suitably the hybrid plasmid pCAR5 consists of the EcoRI-BamHI—DNA fragment which is 23 kb in size (the restriction map in FIG. 1) and the expression vector pBLUESCRIPT-KS+. The hybrid plasmid pCAR6 expediently consists of the PvuII-BamHI DNA fragment which is 1.85 kb in size in FIG. 1 (restriction map) and the expression vector pBLUESCRIPT-KS+.

Expediently the hybrid plasmid pCAR6 is used with promoter $P_{LAC}$, with the expression of the hydrolase gene (rad) being induced with isopropylthiogalactoside (IPTG) according to the host strain.

The hybrid plasmid pCAR6 was deposited both on Jun. 6, 1991, under DSM No. 6551 in *E. coli* XL1-Blue ® and on Apr. 21, 1992, under DSM No. 7053 in *E. coli* DH5, in the Deutsche Sammlung fur Mikroorganismen und Zellkulturen GmbH [German Collection for Microorganisms and Cell Cultures GmbH], Mascheroderweg 1b, D-3300 Brunswick, Germany.

Figure 2:
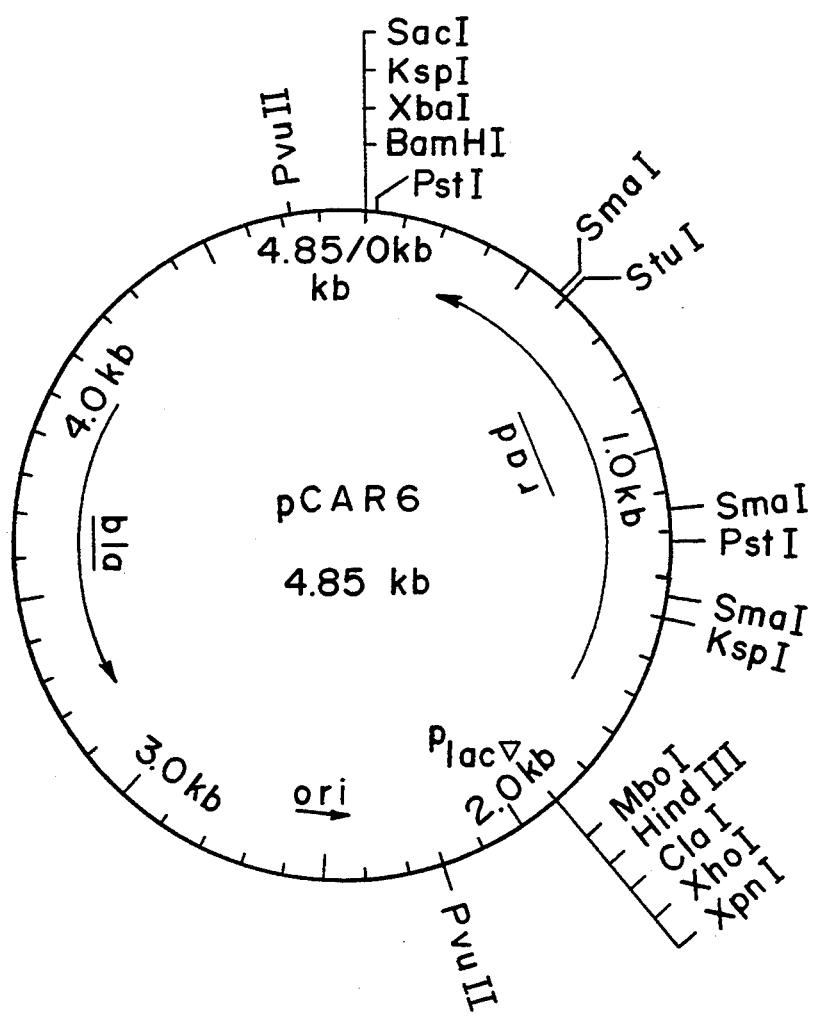
FIG. 2 is a diagram of hybrid plasmid pCAR6.

FIG. 2 shows a diagram of the hybrid plasmid pCAR6.

(D) Host strains

The hybrid plasmids obtained in this way are expediently employed in host strains.

In the case of "broad-host-range" hybrid plasmids, expediently host strains with high substrate and precursor tolerance are employed, such as, microorganisms of genera Pseudomonas, Comamonas, Acinetobacter, Rhizobium, Agrobacterium or Escherichia.

In the case of hybrid plasmids which have a narrow host spectrum, such as, the hybrid plasmid pCAR6, usually the specific host strains in which they grow are employed. Accordingly, microorganisms of the genus Escherichia, especially those of species *E. coli* which are listed in Table 1, are preferably used as the host strains for the hybrid plasmid pCAR6.

(E) Transformation

The transformation of the host strains takes place with the hybrid plasmids of the invention according to known processes. The transformed host strains are then preferably isolated from a selective nutrient medium to which has been added the antibiotic against which the marker gene contained in the hybrid plasmid confers resistance. Accordingly, ampicillin is added to the nutrient medium in the case of the preferred use of the hybrid plasmid pCAR6 which contains the bla gene.

(F) Production Strain

As producer strains according to the invention, all host strains can be used which are transformed with the hybrid plasmid which contains the stereospecific hydrolase gene. Preferably the microorganisms of the species *E. coli*, which are listed in Table 1, and which are transformed with hybrid plasmid pCAR6, as well as their descendants and mutants, are used as producer strains. The microorganisms *E. coli* XL1-Blue (DSM No. 6551) and *E. coli* DH5 (DSM No. 7053) were deposited as already described.

If, for example, from Table 1 *E. coli* MC4100 [described in Mol. Gen. Genet., 192, (1983), pages 293 and 294] is used as the host strain, there is constitutive (permanent) expression of the stereoselective hydrolase gene (rad) under the control of promoter $P_{Lac}$ because of a deletion in the lac-operon (lactose operon) [deletion of (argF - lac) U169]. Accordingly, there is no production of the lac repressor gene lacI (repressor gene negative microorganism). If, for example, from Table 1, *E. coli* K12 (obtainable under DSM No. 498) or *E. coli* HB101 [H. W. Boyer and D. Roulland-Dussoix, J. Mol. Biol., 41, (1969), pages 459 to 472] is used as the host strain, the expression of hydrolase gene (rad) with IPTG is induced because of the presence of the repressor gene lacI (repressor gene positive microorganism).

(G) Biotransformation

According to the invention, for use for the biotransformation, all microorganisms (producer strains) which have been transformed with a gene that produces a stereospecific hydrolase and thus stereospecifically hydrolize R-(−)-2,2-DMCPCA to the acid.

The biotransformation is expediently carried at with microorganisms which are transformed with a hydrolase gene (rad) whose restriction map is represented in FIG. 1. Suitably also used are microorganisms which have been transformed with a DNA fragment (SEQ ID NO: 1) that codes for a polypeptide with stereospecific hydrolase activity, whose amino acid sequence (SEQ ID NO: 2) is represented in FIG. 3. Also suitable are microorganisms which have been transformed with a DNA fragment that hybridizes with the DNA fragment (SEQ ID NO: 1) represented in FIG. 3 and that codes for a with stereospecific hydrolase activity. Especially suitable for the process are, as already described, the microorganisms of the species *E. coli* (Table 1) transformed with the hybrid plasmid pCAR5 or pCAR6, especially those transformed with the hybrid plasmid pCAR6. The cell-free enzymes (the stereospecific hydrolases) from these microorganisms are also suitable. These cell-free enzymes can be obtained by breaking down the microorganism cells in a manner usual to one skilled in the art. For this purpose, for example, the ultrasonic, the French press or the lysozyme methods can be used. These cell-free enzymes can then be immobilized for performing the process on a suitable support material according to methods usual to one skilled in the art.

Preferably the process is carried with resting microorganism cells (not growing cells), which previously have been induced appropriate for their expression system. This means that induction is carried out with IPTG if repressor gene-positive microorganisms, such as, *E. coli* XL1-Blue or *E. coli* DH5, which have been transformed with hybrid plasmid pCAR6, are employed for the process. If, for example, repressor gene-negative (i.e., absence of the repressor gene) microorganisms of species *E. coli*, such as *E. coli* MC4100, are employed for the process, there is permanent (constitutive) expression of the hydrolase gene (rad).

In an especially preferred embodiment, the specific hydrolase activity of the microorganisms is increased with $C_1$–$C_4$ alcohols. For example, methanol, ethanol, propanol, isopropanol or butanol can be used as the $C_1$–$C_4$ alcohols. Preferably methanol or ethanol is used.

The media customary in the art, such as, low molarity phosphate buffers, a mineral salt medium according to Kulla et al. [Arch. Microbiol., 135, (1983), pages 1 to 7] or HEPES-buffer (N-2-hydroxyethylpiperazine-2′-ethanesulfonic acid), can be used as the medium for the process. Preferably, the process is performed in a low molarity phosphate buffer.

Suitably the medium for the biotransformation contains racemic R,S-($\pm$)-2,2-DMCPCA in an amount of 0.2 to 5 percent by weight, preferably 0.2 to 2 percent by weight. Suitably the biotransformation is performed in a range of pH 6 to 11, preferably in a range of pH 6.5 to 10. The temperature for the biotransformation suitably is between 15° and 55° C., preferably between 20° and 40° C. After a normal reaction time of 1 to 30 hours, preferably 5 to 25 hours, R-(−)-2,2-DMCPCA is completely converted to the corresponding acid, resulting in optically pure S-(+)-2,2-DMCPCA is obtained. The S-(+)-2,2-DMCPCA can then be obtained, for example, by extraction, electrodialysis or drying.

Deposit and taxonomic information for *Chromosomol acidovorans* A:18 (DSM No. 6315), *Comamonas acidovorans* TG 308 (DSM No. 6552), *Pseudomonas sp.* NSAK:42 (DSM No. 6433), and microorganism *Bacterium sp.* VIII:II (DSM No. 6316) is set out below.

The pertinent portions of copending U.S. Ser. No. 845,034, filed on Mar. 3, 1992, particularly dealing with the description of DSM No. 6315, DSM No. 6316, DSM No. 6433 and DSM No. 6552, are incorporated herein by reference.

The strains of DSM Nos. 6315 and 6316 were deposited on Jan. 29, 1991, those of DSM No. 6433 on Mar. 25, 1991, and those of DSM No. 6552 on Apr. 6, 1991, with the Deutsche Sammlung von Mikroorganismen und Zellkulturen GmbH (German Collection of Microorganisms and Cell Cultures GmbH), Mascherodeweg 1B, D-3300 Brunswick, Germany.

The scientific (taxonomic) description of *Comamonas acidovorans* A:18 (DSM No. 6315), is:

| | |
|---|---|
| cell shape | rods |
| width micron | 0.5 to 0.7 |
| length micron | 1.5 to 3.0 |
| mobility | + |
| flagella | polar > 1 |
| Gram reaction | − |
| lysis by 3% KOH | + |
| aminopeptidase (Cerny) | + |
| spores | − |
| oxidase | + |
| catalase | + |
| growth | |
| anaerobic | − |
| 37°/41° C. | +/− |
| pH 5.6 | + |
| MacConkey agar | + |
| SS agar | + |
| cetrimide agar | + |
| pigments | |
| nondiffusing | − |
| diffusing | − |
| fluorescent | − |
| pyocyanin | − |
| acid from (OF test) | |
| glucose, aerobic | − |
| glucose, anaerobic | − |
| gas from glucose | − |
| acid from | |
| glucose | − |
| fructose | + |
| xylose | − |
| mannitol | + |
| glycerol | + |
| ONPG | − |
| ADH | − |
| VP | − |
| indole | − |
| NO$_2$ from NO$_3$ | + |
| denitrification | − |
| phenylalaninedesaminase | − |
| levan from saccharose | − |
| lecithinase | − |
| urease | − |
| hydrolysis of | |
| starch | − |
| gelatin | − |
| casein | − |
| DNA | − |
| Tween 80 | − |
| aesculin | − |
| tyrosine catabolism | − |
| use of substrate | |
| acetate | + |
| adipate | + |
| caprate | + |
| citrate | + |
| glycolate | + |
| laevulinate | + |
| malate | + |
| malonate | − |
| phenyl acetate | + |
| L-arabinose | − |
| fructose | + |
| glucose | − |
| mannose | − |
| maltose | − |

| | |
|---|---|
| xylose | − |
| inositol | |
| mannitol | + |
| gluconate | + |
| N-acetylglucosamine | − |
| L-serine | − |
| L-tryptophan | + |
| acetamide | + |
| mesaconate | + |
| citraconate | + |
| L-tartrate | + |
| N-source | |
| NH₄⁺ | ++ |
| R,S-(±)-2,2-DMCPCA | + |
| butyramide | ++ |
| acetamide | + |
| propionamide | + |
| formamide | ± |
| benzamide | + |
| nicotinamide | + |
| API ZONE --- Cs.acidovorans 99.0 percent | |

The scientific (taxonomic) description of *Comamonas acidovorans* TG 308 (DSM No. 6552) is:

| | |
|---|---|
| cell shape | rods |
| Gram reaction (KOH test) | − |
| Gram stain | − |
| spores | − |
| mobility | + |
| °C. growth | |
| 37° C. | + |
| 41° C. | − |
| 45° C. | − |
| catalase | + |
| oxidase | + |
| fermentation in glucose (OF test) | − |

| | isolates TG308 |
|---|---|
| nitrate reduction | + |
| indole production | − |
| acid from glucose | − |
| arginine dehydrolase | − |
| urease | − |
| aesculin hydrolysis | − |
| gelatin hydrolysis | − |
| β-galactosidase | − |
| glucose assimilation | − |
| arabinose assimilation | − |
| mannose assimilation | − |
| mannitol assimilation | + |
| N-acetyl-glucosamine assimilation | − |
| maltose assimilation | − |
| gluconate assimilation | + |
| caprate assimilation | + |
| adipate assimilation | + |
| malate assimilation | + |
| citrate assimilation | − |
| phenyl acetate assimilation | + |
| cytochrome oxidase | + |
| NO₂ from NO₃ | + |
| hydrolysis from urea | − |
| use of fructose | + |
| alkalization of acetamide | + |
| alkalization of tartrate | + |
| alkalization of Simmon's citrate | + |
| alkalization of malonate | (+) |

(+) weakly positive

The scientific (taxonomic) description of *Pseudomonas sp.* NSAK: 42 (DSM No. 6433) is:

| | |
|---|---|
| cell shape | rods |
| width micron | 0.6 to 0.8 |
| length micron | 1.5 to 3.0 |
| mobility | + |
| Gram reaction | − |
| lysis by 3% KOH | + |
| aminopeptidase (Cerny) | + |
| spores | − |
| oxidase | + |
| catalase | + |
| growth | |
| anaerobic | − |
| 37°/41° C. | +/− |
| pH 5.6 | + |
| MacConkey agar | + |
| SS agar | − |
| cetrimide agar | − |
| pigments | yellow |
| acid from (OF test) | |
| glucose, aerobic | − |
| glucose, anaerobic | − |
| gas from glucose | − |
| acid from | |
| glucose | − |
| fructose | − |
| xylose | − |
| ONPG | − |
| ODC | − |
| ADH | − |
| VP | − |
| indole | − |
| NO₂ from NO₃ | − |
| denitrification | − |
| phenylalaninedesaminase | − |
| levan from saccharose | − |
| lecithinase | − |
| urease | − |
| hydrolysis of | |
| starch | − |
| gelatin | − |
| casein | − |
| DNA | − |
| Tween 80 | − |
| aesculin | − |
| tyrosine catabolism | − |
| growth material requirement | − |
| use of substrate | |
| acetate | + |
| caprate | + |
| citrate | + |
| glycolate | + |
| lactate | + |
| laevulinate | + |
| malate | + |
| malonate | + |
| phenyl acetate | + |
| suberate | + |
| L-arabinose | − |
| fructose | + |
| glucose | − |
| mannose | − |
| maltose | − |
| xylose | − |
| mannitol | − |
| gluconate | + |
| 2-ketogluconate | + |
| N-acetylglucosamine | − |
| L-serine | + |
| L-histidine | + |
| hydroxybutyrate | + |
| N-source | |
| NH₄⁺ | ++ |
| R,S-(±)-2,2-DMCPCA | + |

The scientific description of *Bacterium sp.* VIII:II (DSM No. 6316), is:

| | |
|---|---|
| Gram stain | + |
| Gram reaction (KOH test) | − |
| oxidase | − |
| catalase | − |

-continued

| | |
|---|---|
| nitrate reduction | − |
| tryptophan → indole | − |
| glucose (anaerobic) | − |
| arginine | − |
| urease | − |
| aesculin | + |
| gelatin | − |
| β-galactosidase | + |
| glucose | + |
| arabinose | − |
| mannose | (+) |
| mannitol | + |
| N-acetylglucosamine − | − |
| maltose | + |
| gluconate | − |
| caprate | − |
| adipate | − |
| malate | − |
| citrate | − |
| phenyl acetate | − |

SOUTHERN BLOTTING AND HYBRIDIZATION

DNA fragments are separated on agarose gels and denatured in situ. The fragments are then transferred from the gel to a solid support (either nitrocellulose filters or nylon membranes), where they are immobilized. After prehybridization to reduce nonspecific hybridization with the probe, the filter or membrane is hybridized to the desired radiolabeled nucleic acid probe. The filter or membrane is washed to remove unbound and weakly binding probe, and is then autoradiographed. A convenient alternative approach, in which oligonucleotides are hybridized directly to the DAN denatured in the gel, is also described.

Short Protocol

Southern Blotting And Hybridization Using Nitrocellulose Filters

1. Digest samples (remember marker).
2. Prepare an agarose gel, load samples, and electrophorese.
3. Stain 30 min using 25 µl of 10 mg/ml ethidium bromide per 500 ml water. Photograph gel (with ruler).
4. Acid treat with 0.2N HCl for 10 min.
5. Decant acid and rinse gel several times with water.
6. Add 500 ml denaturation solution for 15 min. Decant solution and repeat.
7. Decant denaturation solution and add 500 ml neutralization solution for 30 min.
8. Measure gel and set up overnight transfer:
   Wick in tray with 20×SSC
   Gel
   Nitrocellulose (soaked in H$_2$O and 20×SSC)
   3MM Whatman filter paper
   Paper towels
   Weight
9. Dissemble transfer pyramid and rinse nitrocellulose in 2×SSC for 5 min.
10. Bake nitrocellulose at 80° C. for 2 hr.
11. Add 6 to 10 ml prehybridization solution and prehybridize overnight.
12. Prepare labeled nucleic acid probe. Add 500,000 cpm of of the probe/ml hybridization solution. Remove prehybridization solution and add 6 to 10 ml hybridization solution. Hybridize overnight.
13. Wash twice, 15 min each, in 1×SSC, 0.1% SDS at room temperature. Wash twice, 15 min each, in 0.25×SSC, 0.1% SDS at hybridization temperature.
14. Expose to X-ray film.

EXAMPLE 1

1.1 Preparation of the Chromosomol DNA of Comamonas Acidovorans A:18

The chromosomal DNA of a fresh overnight culture of Comamonas acidovorans A:18 (100 ml of nutrient yeast broth, 30° C.) was isolated by the modified methods of R. H. Chesney et al. [J. Mol. Biol., 130, (1979), pages 161 to 173]:

The cells were spun down (15 min, 6500×g, 4° C.) and resuspended in tris-HCl-buffer (2.25 ml, 0.05 mol/l), pH 8.0, 10 percent (w/v) sucrose. After the addition of 375 µl of lysozyme solution (10 mg/ml, 0.25 mol/l tris-HCl-buffer, pH 8.0) and 900 µl of 0.1 mol/l EDTA, pH 8.0, the suspension was cooled on ice for 10 minutes. Then followed the addition of 450 µl of 5 percent (w/v) SDS and 50 µl of ribonuclease (10 mg/ml H$_2$O), and an incubation at 37° C. for 30 min. The incubation was continued after the addition of a spatula tip full of proteinase K and 400 µl of pronase (20 ml/ml H$_2$O) for 2 hours. It was centrifuged after mixing with 4.3 g of CsCl (30 min., 40,000×g, 20° C.), mixed with 250 µl of ethidium bromide (10 mg/ml), and centrifuged in an ultracentrifuge (VTi 65.2-tube) (more than 8 hours, 246,000×g, 20° C.). The DNA band was aspirated out of the tube by means of long-wavelength UV light. After addition of the 4-times the volume of TE-buffer (10 mmol/l tris-HCl, pH 8.0, 1 mmol/l EDTA), the ethidium bromide was extracted three times with n-butanol saturated with water. The DNA was precipitated with isopropanol, taken up in TE-buffer and incubated for 15 minutes at 65° C. The preparation can be stored at 4° C.

1.2 Restriction and Ligation of Chromosomal DNA

5 µg of Comamonas acidovorans A:18 (DSM No. 6315)-DNA and 4.5 µg of Vector-DNA (pBLUESCRIPT-KS+ ®) were each cut (6.5 hours at 37° C.) with 20 units of restriction enzyme EcoRI in a total volume of restriction buffer of 100 µl. The DNAs were precipitated with ethanol and dried in a Speed Vac ® concentrator. The precipitates were taken up in the ligation buffer [20 mmol/l tris-buffer, 10 mmol/l DTT (dithiothreitol), 10 mmol/l MgCl$_2$, 0.6 mol/l ATP (adenosine triphosphate, pH 7.2], and combined (ligation volume 100 µl). After the addition of 1 unit of T4-DNA-ligase, it was incubated overnight at 13° C. The DNA of the ligation mixture was precipitated with isopropanol and taken up in 30 µl of water for transformation.

1.3 Transformation of E. coli XL1-Blue ® and Selection

Competent cells of E. coli XL1-Blue ® were transformed by electroporation with the ligation mixture using the method described by S. Fiedler and R. Wirth [Analyt. Biochem., 170, (1988), pages 38 to 44]. For plasmid detection, nutrient agar with ampicillin (100 µg/ml) was selected and for insert detection with 0.5 mmol/l IPTG (isopropyl-β-D-thiogalactoside) and x-Gal (30 µg/ml, 5-bromo-4-chloro-3-indolyl-β-D-galactopyranoside) was used with incubation in 37° C. At a transforation sequence of 1.7×10$^8$ cfu/ml ("colony forming units" ie., live cells), almost all of the clones had an EcoRI-"insert".

EXAMPLE 2

2. Screening of *Comamonas Acidovorans* A:18-Gene Bank According to the R-specific Amidase Gene Clones with hybrid plasmids (EcoRI-insert) were examined for their growth capabilities on minimal medium agar according to H. Kulla et al. [Arch. Microbiol., 135, (1983), pages 1 to 7] with 0.2 percent (v/v) of glycerol as the C-source, 0.15 percent (w/v) of R,S-($\pm$)-2,2-DMCPCA as the sole N-source, and 0.5 mmol/l of IPTG as the inducer of the lac promoter, as well as ampicillin (5 µg/ml) for plasmid stabilization. Only clones, which contain the intact hydrolase gene rad on the DNA insert in the plasmid, were able to use R-(−)-2,2-DMCPCA as the N-source, to convert the latter into the R-acid which was sought, and to grow on this minimal medium. All of the clones selected in this way contained a hybrid plasmid composed of vector pBLUESCRIPT-KS+ ® vector with an EcoRI-"insert" of about 23 kb. The plasmid pCAR1 was isolated and more closely characterized.

EXAMPLE 3

3.1 Isolation of the R-specific Hydrolase from *Comamonas acidovorans* A:18 and N-terminal Peptide Analysis (a) Preparation of Cell-Free Extract 16 liters of a cell suspension of *Comamonas acidovorans* A:18 (DSM No. 6315) was concentrated to 700 ml ($OD_{650}=33.5$) with a hydrolase activity at 37° C. of 0.6 g of R-(−)-2,2-DMCPCS/l/h/optical density at 650 nm ($OD_{650}$) = 1, that was previously induced with R,S-($\pm$)-DMCPCA. Then the cells were centrifuged several times, resuspended in HEPES-buffer, and then taken up in HEPES-buffer (40 ml). The volume of the total cell suspension was then 95 ml ($OD_{650}=210$). The hydrolase activity was determined at 30° C. and was 0.34 g of product/l/h/$OD_{650}=1$. Then the cells were broken down twice in the French press at a pressure of 1200 bars. To obtain a cell-free extract, this suspension was centrifuged at 20000×g for 20 min. 50 ml of extract was obtained with a protein amount (measured according to the Bradford method) of 39.3 mg/ml and with a hydrolase activity at 30° C. of 12.5 g of R-(−)-2,2-DMCPCS/l/h/mg of protein.

(b) Chromatography

This crude-cell extract (50 ml) was applied to a column filled with Q-Sepharose (Pharmacia) which was equilibrated against a HEPES-buffer (0.1 mol/l, pH 7.5). This column was flushed twice more with the same buffer and then the proteins were eluted with a HEPES-buffer-gradient (0.1–1 mol/l). Altogether 140 ml of protein solution with hydrolase activity was eluted with HEPES-buffer (1 mol/l) that was then concentrated by ultrafiltration (Amicon membrane YM10). The amount of protein of this enzyme solution was 131 mg/ml and the hydrolase activity was 1 µmol/min/ng of protein. Then 2 ml of this protein solution was applied to a column with Superose-12 (Pharmacia) which had been equilibrated against a HEPES-buffer (0.1 mol/l, pH 7.5). With this buffer altogether 36 ml of protein solution was eluted. The latter was also concentrated by ultrafiltration (Amicon membrane YM10). The amount of protein was 20.1 mg/ml and the hydrolase activity was 1.2 µmol/min/ng of protein. The thus-obtained protein solution was then applied to a column with anion exchanger Li Chirospher 2000 TMAE (trimethylammoniumethyl salt) (Merck) which was equilibrated against a HEPES-buffer (0.1 mol/l, pH 7.5). After flushing of the column with the same buffer, the protein solution was eluted with a NaCl gradient (0–1 mol/l) in the same buffer. The protein concentration was 15 mg/ml and the hydrolase activity were 1.2 µmol/min/ng of protein.

(c) Identification of the Hydrolase by 1- and 2-Dimensional Electrophoresis

In the crude-cell extract the hydrolase protein was identified by SDS-PAGE. At the same time non-induced cell extract was compared with induced cell extract on the SDS-PAGE (induction with R,S-($\pm$)-2,2-DMCPCA). A protein band with a molecular weight around 46000 was detected in the induced cell extract. The protein fractions obtained by chromatography with hydrolase activity were also analyzed by SDS-PAGE. The protein with a molecular weight of about 46000 was concentrated by this chromatographic purification and it was concentrated after the third chromatography to about 80 percent. This 80 percent pure sample was then analyzed by two-dimensional electrophoresis (2-D SDS-PAGE). By this method a protein "spot" with a molecular weight of about 46000, which corresponded to the hydrolase, was able to be detected.

(d) Sequencing

The protein "spot" obtained by 2-D SDS-PAGE was then blotted on a PVDF (polyvinylidene difluoride) membrane and cut out from the membrane. Then this protein was directly sequenced according to the method of Hochstrasser et al. [Applied and Theoretical Electrophoresis, 1, (1988), pages 73 to 76, "HDL particle-associated proteins in plasma and cerebrospinal fluid"]. 21 amino acids (AS) of the N-terminal amino acid sequence was identified by this method.

EXAMPLE 4

4. Localization of the Hydrolase Gene (rad) of the Cloned EcoRI Fragment 4.1 Rough Restriction Map of pCAR1

A rough restriction map of pCAR1 relative to EcoRV, PVuII, KspI, SmaI, PstI, StuI and BamHI was made by restriction analysis according to a conventional process [Current Protocols Molecular Biology, John Wiley and Sons, New York, (1987), section 2].

4.2 Formulation of Mixed DNA-oligomers Based on the N-terminal Peptide Sequence of the Hydrolase Because of the genetic code, two mixed DNA oligomers were able to be formulated for the N-terminal peptide sequence of *Comamonas acidovorans* A:18 hydrolase and synthesized with a DNA-synthesis machine.

DNA-oligomer (mixture)

See FIG. 4.

DNA-Antisense oligomer mixture)

See FIG. 5.

4.3 Southern Blot-Hybridization of Restriction Fragments Of Plasmid pCAR1

The DNA fragments separated by agarose gel electrophoresis (0.6 percent), which were obtained according to various restrictions (BamHI, PstI, EcoRI) or pCAR1, were transferred by the known Southern Blot process to nitrocellulose [Current Protocols in Molecular Biology, John Wiley and Sons, New York, (1987), section 2.9 ff].

The DNA-oligomers were end labeled in the same way with [$^{32}$P]-gamma-ATP:

400 ng of DNA-oligomer, 22 $\mu$Ci$^{32}$P-Gamma-ATP, and 11 units of polynucleotide kinase phosphate-free, in a total of 25 $\mu$l of polynucleotide kinase-buffer (0.05 mol/l tris-HCl, pH 7.5, 0.01 mol/l MgCl$_2$, 5 mmol/l DTT) were incubated for 30 minutes at 37° C.

This was followed by purification by Sephadex G-25 gel filtration (Pharmacia) and hybridization against the Southern Blots according to the known process (in the above-mentioned reference).

By hybridization with the nucleotide-oligomers corresponding to the N-terminal protein sequence, it is possible to label an EcoRI-BamHI DNA fragment which is 2.3 kb in size or an PvuII-BamHI DNA fragment which is 1.85 kb in size on the hybrid plasmid pCAR1.

4.4 Subclonings of the Hydrolase Gene (rad)

The 2.3 kb EcoRI-BamHI DNA fragment of the 1.85 kb PvuII-BamHI DNA fragment, which codes for the R-specific hydrolase from Comamonas acidovorans A:18, was inserted into vector DNA pBLUESCRIPT-KS+ ® or pBLUESCRIPT-SK+ ® digested in the same way. The desired hydrolase activity only shows an orientation of the insert toward promoter P$_{Lac}$ in the clones after IPTG induction. The vector pBLUES-CRIPT-KS+ ® with the 2.3 kb EcoRI-BamHI DNA fragment was designated as hybrid plasmid pCAR6. Vector pBLUESCRIPT-KS+ ® with the 1.85 kb PvuII-BamHI DNA fragment was designated hybrid plasmid pCAR5.

EXAMPLE 5

5. Determination of Activity of R-(−)-2,2-DMCPCA Hydrolase

The microorganism suspension was adjusted to an optical density of 0.5 at 650 nm for the determination of the hydrolase activity. A phosphate buffer (10 mmol/l), pH 7.0, with 0.2 percent by weight of R-(±)-2,2-DMCPCA served as the medium. This suspension was incubated for 4 hours at 30° C. with shaking. The NH$^+_4$ released by the hydrolase or the R-(−)-2,2-DMCPCS was measured and the activity was expressed as g of R-(−)-2,2-DMCPCA converted per l/h/optical density at 650 nm, provided that 1 mmol of formed NH$^+_4$=1 mmol corresponds to the reacted R-(−)-2,2-DMCPA.

EXAMPLE 6

Production of S-(+)-2,2-DMCPCA

E. coli K12 with hybrid plasmid pCAR6, in the mineral salt medium containing 0.2 percent (v/v) of glycerol and 0.15 percent by weight of R,S-(±)-2,2-DMCPCA, showed a specific hydrolase activity of 1.2 g of R-(−)-2,2-DMCPCS/l/h/OD$_{650}$ after IPTG-induction. The reaction of R-(−)-2,2-DMCPCA to R-(−)-acid was confirmed by NH$^+_4$ release and GC analysis. The target product S-(+)-2,2-DMCPCA remained unchanged in the racemic mixture.

Corresponding to E. coli K12, the microorganisms listed in Table 1 were cultivated and the results are shown in Table 1.

TABLE 1

| Strain | Stereospecific Hydrolase Activity In Various E. Coli Strains | | | | |
|---|---|---|---|---|---|
| | Specific Activity g/l/h/OD | Factor | Stability in % (4) | Max. OD$_{650nm}$ | Total Activity g/l/h |
| Comamonas acidovorans A:18[1] (not according to the invention) | 0.5 | 1 | — | 6 | 3.0 |
| E. coli K12/pCAR6[2] | 1.2 | 2.4 | 90 | nt | — |
| E. coli HB101/pCAR6[3] | 0.25 | 0.5 | nt | nt | — |
| E. coli MC4100/pCAR6[3] | 0.53 | 1 | 89 | nt | — |
| E. coli XL1BLUE/pCAR6[5] (DSM No. 6551) | 0.5 | 1 | 90 | 30 | 15.0 |
| E. coli DH5/pCAR6[5] (DSM No. 7053) | 2.1 | 4.2 | 100 | 30 | 63.0 |

Notes:
[1]induction with amide
[2]induction with IPTG
[3]constitutive
[4]plasmid stability after 24 hours with selection of antibioties, nt = not tested
[5]without induction

EXAMPLE 7

Activity Test With C$_1$-C$_4$ alcohols

The activity tests were performed first with Comamonas acidovorans A:18 at 37° C. with 0.5 percent R,S-(±)-2,2-DMCPCA in 10 mM of potassium phosphate buffer at pH 7.0. The control was without a solvent; the test studies were with 5 to 16 volume percent of solvent. The computation of the specific activity took place as described in Example 5.

| Solvent (Volume percent) | Activity for the reaction of g R,S-(±)-2,2-DMCPCA/l/h/OD$_{650}$ nm |
|---|---|
| — | 0.64 |
| Ethanol (10) | 1.24 |
| Isopropanol (10) | 1.85 |
| Methanol (5) | 1.79 |
| Methanol (10) | 1.54 |
| Methanol (16) | 1.66 |

In biotransformations in the 20 l-fermenter with 2 to 3 percent R,S-(±)-2,2-DMCPCA (37° C., 10 mM, potassium phosphate buffer, pH 7.0) with the addition of 5 to 7.5 volume percent of methanol or ethanol, a shortening of the reaction time and a higher yield of S-(+)-2,2-DMCPCA (selectivity enhancement) was achieved.

The same effect was observed in the E. coli-strain XL1-Blue with the hydrolase gene. The results are compiled in Table 2.

TABLE 2

[The same activities (in water) were used for each strain.]

| Strain | R,S-2,2-DMCPCA (%) | Solvent (Vol. %) | Time (h) | ee (%) | Yield (%)* |
|---|---|---|---|---|---|
| A:18 | 2.0 | — | 22 | 99 | 41.5 |
| A:18 | 2.3 | Methanol (7.5) | 15 | 99.2 | 47 |
| XL1/pCAR6 | 2.8 | — | 24 | 100 | 36 |
| XL1/pCAR6 | 2.8 | Methanol (7.5) | 7 | 98.2 | 46 |
| XL1/pCAR6 | 2.8 | Ethanol (5) | 7 | 98.6 | 44 |

Note:
*of S-(+)-2,2-DMCPCA relative to the R,S-DMCPCA used.

EXAMPLE 8

Immobilization of the Stereospecific Hydrolase of E. coli XL1-Blue/pCAR6

The cell-free extract (288 ml) of E. coli XL1-Blue/pCAR6 containing 28 mg of protein/ml with a hydrolase activity at 37° C. of 0.29 μmol R-(−)-2,2-DMCPCA/min.mg of protein was first prepurified by column chromatography on Q-Sepharose (Pharmacia). The hydrolase protein was eluted with a NaCl-gradient (0–1 mol/l) in a tris-HCl buffer (0.1 molar, pH 7.5). The protein with hydrolase activity, which had been eluted between 40 percent and 80 percent of the NaCl-gradient, then was concentrated by ultrafiltration (Amicon membrane YM10) and desalinated by gel filtration (PD-10, Sephadex G-25M, Pharmacia LKB). The end weight was then 67 mg of protein/ml containing 47 ml in potassium phosphate buffer (0.1 molar, pH 7.0) with a hydrolase activity at 37° C. of 0.69 μmol R-(−)-2,2-DMCPCA/min.mg of protein. Then this prepurified stereospecific hydrolase was immobilized on Eupergit C as the carrier material (Rohm Pharma GmbH, Weiterstadt, FRG). In this connection the oxirane groups of the insoluble carrier material were covalently bound to the free amino groups of the hydrolase protein. The immobilization was performed for 90 hours at room temperature in potassium phosphate-buffer (1 molar, pH 8.5). 10.2 mg of immobilized protein/g moist weight of Eupergit C with a hydrolase activity at 37° C. of 1.5 μmol of R-(−)-2,2-DMCPCA/min.g moist weight of Eupergit C was obtained. The stability of the immobilized hydrolase at 37° C. in the potassium phosphate buffer (10 molar, pH 8.5), containing 0.5 percent by weight of R,S-(±)-2,2-DMCPCA, is represented in Table 3.

TABLE 3

| Time, hours | Activity of the immobilized hydrolase [μmol R-(-)-2,2-DMCPCA/min.g moist weight of Eupergit C] |
|---|---|
| 0–90 | 1.5 |
| 90–185 | 0.68 |

What is claimed is:

1. A microbiological process for the production of S-(+)-2,2-dimethylcyclopropanecarboxamide, characterized in that R-(−)-2,2-dimethylcyclopropanecarboxamide in racemic R,S-(±)-2,2-dimethylcyclopropanecarboxamide is biotransformed by means of microorganisms which are transformed with a gene isolated from the genus Comamonas that produces a stereospecific hydrolase and which is characterized by the restriction map which is represented in FIG. 1, into R-(−)-2,2-dimethylcyclopropanecarboxylic acid, optically active S-(+)-2,2-dimethylcyclopropanecarboxamide being obtained, and the optically active S-(+)-2,2-dimethylcyclopropanecarboxamide is isolated.

2. The process according to claim 1 wherein the biotransformation is performed with microorganisms, which have been transformed with a DNA fragment (SEQ ID NO: 1), which codes for a polypeptide with stereospecific hydrolase activity and whose amino acid sequence (SEQ ID NO: 2) is represented in FIG. 3.

3. The process according to claim 2 wherein the biotransformation is performed with microorganisms, which have been transformed with a DNA fragment, which hybridizes under conditions effective to achieve such hybridization and has at least a homology with the DNA fragment (SEQ ID NO: 1) of 90 percent which is represented in FIG. 3 and which codes for a polypeptide with stereospecific hydrolase activity.

4. The process according to claim 3 wherein the biotransformation is performed with microorganisms of genus Escherichia, Pseudomonas, Comamonas, Acinetobacter, Rhizobium or Agrobacterium.

5. The process according to claim 4 wherein the biotransformation is performed with microorganisms of the species *Escherichia coli*.

6. The process according to claim 5 wherein the biotransformation is performed with microorganisms of the strain *Escherichia coli* XL1-Blue (DSM No. 6551), which has been transformed with the hybrid plasmid pCAR6, or a descendant thereof that performs said biotransformation and maintains the defining characteristics of the microorganism, or a mutant thereof that performs said biotransformation and maintains the defining characteristics of the microorganisms.

7. The process according to claim 5 wherein the biotransformation is performed with microorganisms of the strain *Escherichia coli* DH5 (DSM No. 7053), which has been transformed with the hybrid plasmid pCAR6, or with a descendant thereof that performs said biotransformation and maintains the defining characteristics of the microorganisms, or a mutant thereof that performs said biotransformation and maintains the defining characteristics of the microorganism.

8. The process according to claim 7 wherein the biotransformation is performed in a medium containing racemic R,S-(±)-2,2-dimethylcyclopropanecarboxamide in an amount of 0.2 to 5 percent by weight.

9. The process according to claim 8 wherein the biotransformation is performed at a pH of 6 to 11 and a temperature of 15° to 55° C.

10. The process according to claim 2 wherein the biotransformation is performed with microorganisms of genus Escherichia, Pseudomonas, Comamonas, Acinetobacter, Rhizobium or Agrobacterium.

11. The process according to claim 2 wherein the biotransformation is performed in a medium containing racemic R,S-($\pm$)-2,2-dimethylcyclopropanecarboxamide in an amount of 0.2 to 5 percent by weight.

12. The process according to claim 2 wherein the biotransformation is performed at a pH of 6 to 11 and a temperature of 15° to 55° C.

13. A DNA isolate from genus Comamonas coding for a stereospecific hydrolase characterized by the restriction map which is represented in FIG. 1.

14. An isolated DNA fragment coding for a polypeptide with stereospecific hydrolase activity whose amino acid sequence (SEQ ID NO: 2) is represented in FIG. 3.

15. An isolated DNA fragment that hybridizes under conditions effective to achieve such hybridization and has at least a homology with the DNA fragment (SEQ ID NO.: 1) of 90 percent which is represented in FIG. 3 and which codes for a polypeptide with stereospecific hydrolase activity.

16. A hybrid plasmid consisting of an expression vector with the DNA or the DNA fragment inserted in it according to claims 13, 14 or 15.

17. Hybrid plasmid pCAR6 consisting of the DNA or the DNA fragment according to claims 13, 14 or 15 and expression vector pBLUESCRIPT-KS+.

18. A microorganism that has been transformed with a hybrid plasmid selected from the group consisting of (a) a hybrid plasmid consisting of an expression vector with the DNA or the DNA fragment inserted in it according to claims 13, 14 or 15, (b) a hybrid plasmid pCAR6 consisting of the DNA or the DNA fragment according to claims 13, 14 or 15 and expression vector pBLUESCRIPT-KS+, deposited in *Escherichia coli* XL1-Blue (DSM No. 6551), or (c) and a hybrid plasmid pCAR6 consisting of the DNA or the DNA fragment according to claims 13, 14 or 15 and expression vector pBLUESCRIPT-KS+, deposited in *Escherichia coli* DH5 (DSM No. 7053).

19. A microorganism according to claim 18 of the strain *Escherichia coli* XL1-Blue (DSM No. 6551) that has been transformed with hybrid plasmid pCAR6, or a descendant thereof or a mutant thereof that each performs the biotransformation of R-(−)-2,2-dimethylcyclopropanecarboxamide in racemic R,S-($\pm$)-2,2-dimethylcyclopropanecarboxamide into R-(−)-2,2-dimethylcyclopropanecarboxylic acid, optically active S-(+)-2,2-dimethylcyclopropanecarboxamide being obtained, and that each maintains the defining characteristics of the microorganism.

20. A microorganism according to claim 18 of the strain *Escherichia coli* DH5 (DSM No. 7053) that has been transformed with hybrid plasmid pCAR6, or a descendant thereof or a mutant thereof that each performs the biotransformation of R-(−)-2,2-dimethylcyclopropanecarboxamide in racemic R,S-($\pm$)-2,2-dimethylcyclopropanecarboxamide into R-(−)-2,2-dimethylcyclopropanecarboxylic acid, optically active S-(+)-2,2-dimethylcyclopropanecarboxamide being obtained, and that each maintains the defining characteristics of the microorganism.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1843 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Comamonas acidovorans
        ( B ) STRAIN: A:18

( i x ) FEATURE:
        ( A ) NAME/KEY: miscfeature
        ( B ) LOCATION: 289..1566

( x ) PUBLICATION INFORMATION:
        ( H ) DOCUMENT NUMBER: IE 9224406
        ( I ) FILING DATE: 23-JUL-1992
        ( K ) RELEVANT RESIDUES IN SEQ ID NO:1: FROM 1 TO 1843

( x ) PUBLICATION INFORMATION:
        ( H ) DOCUMENT NUMBER: JP 198717/92
        ( I ) FILING DATE: 24-JUL-1992
        ( K ) RELEVANT RESIDUES IN SEQ ID NO:1: FROM 1 TO 1843

( x ) PUBLICATION INFORMATION:
        ( H ) DOCUMENT NUMBER: PL P 295408
        ( I ) FILING DATE: 24-JUL-1992
        ( K ) RELEVANT RESIDUES IN SEQ ID NO:1: FROM 1 TO 1843

( x ) PUBLICATION INFORMATION:
        ( H ) DOCUMENT NUMBER: RO 92-01033
        ( I ) FILING DATE: 24-JUL-1992
        ( K ) RELEVANT RESIDUES IN SEQ ID NO:1: FROM 1 TO 1843

( x ) PUBLICATION INFORMATION:
    ( H ) DOCUMENT NUMBER: SU UNKNOWN
    ( I ) FILING DATE: 24-JUL-1992
    ( K ) RELEVANT RESIDUES IN SEQ ID NO:1: FROM 1 TO 1843

( x ) PUBLICATION INFORMATION:
    ( H ) DOCUMENT NUMBER: CS PV2323- 92
    ( I ) FILING DATE: 24-JUL-1992
    ( K ) RELEVANT RESIDUES IN SEQ ID NO:1: FROM 1 TO 1843

( x ) PUBLICATION INFORMATION:
    ( H ) DOCUMENT NUMBER: HU P9202439
    ( I ) FILING DATE: 24-JUL-1992
    ( K ) RELEVANT RESIDUES IN SEQ ID NO:1: FROM 1 TO 1843

( x i ) SEQUENCE DESCRIPTION: SEQ ID NO:1:

| | | | | | | |
|---|---|---|---|---|---|---|
| AGCTGCGGTT | GCAGGCCAGC | CGCCAGCGCC | TGATGCAGGG | GCGCTGCTCC | AGCGTGACCG | 60 |
| AGGCGGCCTT | CGCGCATGGG | TTCTCCGATG | CGGCGCACTT | CAGCCGAGCC | TTTCGCAAGG | 120 |
| CGTTCGGCTG | CACGCCCCGC | AGCCTGCTGG | CCGCCTGAGC | AAGGTCGCTG | ACCTCACGAA | 180 |
| CAAGCGTCGG | CGCCGCCGGC | TCCCTAGCAT | GGGCCTGCCG | TGCGTCCCGT | GCGGCTTTTC | 240 |
| CAGTGCAACA | ACGGTGGCGC | CCCGGAGCCG | GGCGCCGGGA | GACATGCCAT | GAATGACAGC | 300 |
| GAACTGCACC | ATCTCGAACT | GCTGGAGGTG | GGGCGCGAGA | TCCAGTCCCG | CCGCATTTCG | 360 |
| TCGGAAGAGG | TGACCCGCCA | CATGCTGGCG | CGCATCGAGG | CCGTGGACGC | GCGGCTGCAC | 420 |
| AGCTACGTGA | CGGTGATGGC | GCAGCAGGCG | ATGGAGGACG | CCCGCCGCGC | CGACGCCGAG | 480 |
| ATCGCGCAGG | GCGCCGCCGC | GGTGCGCTGC | ACGGCGTGCC | GTGGCGCTCA | AGGACCTGCT | 540 |
| GTGGACCCGG | GGCGTCCCCA | CCACGCATGG | AATGACGCTG | CACCGCGACC | ATCGCCCCAC | 600 |
| GGAAGATGCC | ACCGTGGTGC | GCAGGCTGCG | CGAGGCCGGC | GCCGTCATCC | TGGGCAAGCT | 660 |
| GCAGCAGACC | GAAGGCGCCT | TCGCCGACCA | CCATCCCGAG | ATCACTGCCC | CCGTCAACCC | 720 |
| CTGGAGCGCC | CAGCTATGGC | CCGGGGCCTC | GTCCAGCGGC | TCGGGCGTGG | CCACGGCGGC | 780 |
| GGGGCTGTGC | TTCGGATCGC | TGGGCACGGA | CACCGGGGGC | TCCATCCGCT | TTCCATCGGC | 840 |
| CGCCAACGGC | ATCACGGGGC | TCAAGCCCAC | CTGGGGCAGG | GTGAGCCGCC | ACGGCGCCTT | 900 |
| CGAACTGGCC | GCGTCCCTGG | ACCACATAGG | CCCGATGGCG | CGCAGTGCTG | CCGATGCCGC | 960 |
| AGCCATGCTC | GCGGCCATCG | CCGGGGCGGA | CCCGCTGGAC | CCTACGGCCA | GCCAGTGCAG | 1020 |
| CGTGCCCGAC | TATCTGGCCA | TGATGACGCG | CGGATTCTCC | GGCCTGCGCC | TGGGCATGGA | 1080 |
| CCGGCAATGG | GCACTGGACG | GCGTGGATGC | CCCCTCCCGC | CAGGCGGTGG | AGCAGGCCCT | 1140 |
| GGCGGTGGCG | CAGCGCCTGG | GGGCCAGCGT | GCAGGAGGTC | CGCTTTCCCG | ATGCCACCCA | 1200 |
| GGCGGTGGAG | GACTGGCCGG | CGCTGTGCGC | GGTGGAGACC | GCCGTGGCGC | ACGGCGCCAC | 1260 |
| GTTCCCTGCA | CGGCGCGAGG | CCTATGGCCC | CGGGCTCGCC | GGGTTGATCG | ACCTGGGGCT | 1320 |
| GGGCCTGTCC | GCCACCGACT | ACCAGCGGCT | GCTGCTGCGC | CGCGCGGACT | TCACGGGCCG | 1380 |
| GGTGCGTGCA | CTCTTCGCGC | AGGTGGATCT | GCTGCTGGTC | CCCGCCACGG | CCTTTGCGGC | 1440 |
| CCCCACGCTG | CAACGCATGG | CGCATTTCGG | CTCCGATGCC | GAGCTGTTCT | CGGGCATGCT | 1500 |
| GCGCTACACC | TGCCCGTTCG | ACCTCACGGG | CAGCCCCACG | ATCACGCTGC | CGGCGGACG | 1560 |
| CACTTCTGAG | GGCGCGCCCG | TGGCCTTCCA | GTTCGTGGCC | CCCGACTTCC | GCGAAGACCT | 1620 |
| GCTGGTGCGC | GCGGGCTGGG | CGTTCCAGCA | GGCCACGGAC | TGGCACAGAC | AGCACCCTGC | 1680 |
| TGCCTGAGCT | GCCTGAGCCG | CCAGGCCGGT | GGCGCGACAC | GGGCCTGTCA | CACAGCCTTC | 1740 |
| CTAGACTGGC | GTGATGTCCT | TGATCGAGAT | GGAAGGTGTC | GCCAAGTCCT | GGGGCGGCAC | 1800 |
| CACGGCGCTG | CAGGCGCTGG | ATCTGCGCAT | TGAACCCGGA | TCC | | 1843 |

( 2 ) INFORMATION FOR SEQ ID NO:2:

( i ) SEQUENCE CHARACTERISTICS:
    ( A ) LENGTH: 426 amino acids
    ( B ) TYPE: amino acid
    ( D ) TOPOLOGY: linear ( x ) PUBLICATION INFORMATION:
    ( H ) DOCUMENT NUMBER: IE 9224406
    ( I ) FILING DATE: 23-JUL-1992
    ( K ) RELEVANT RESIDUES IN SEQ ID NO:2: FROM 1 TO 426

( x ) PUBLICATION INFORMATION:
    ( H ) DOCUMENT NUMBER: JP 198717/92
    ( I ) FILING DATE: 24-JUL-1992
    ( K ) RELEVANT RESIDUES IN SEQ ID NO:2: FROM 1 TO 426

( x ) PUBLICATION INFORMATION:
    ( H ) DOCUMENT NUMBER: PL P 295408
    ( I ) FILING DATE: 24-JUL-1992
    ( K ) RELEVANT RESIDUES IN SEQ ID NO:2: FROM 1 TO 426

( x ) PUBLICATION INFORMATION:
    ( H ) DOCUMENT NUMBER: RO 92-01033
    ( I ) FILING DATE: 24-JUL-1992
    ( K ) RELEVANT RESIDUES IN SEQ ID NO:2: FROM 1 TO 426

( x ) PUBLICATION INFORMATION:
    ( H ) DOCUMENT NUMBER: SU UNKNOWN
    ( I ) FILING DATE: 24-JUL-1992
    ( K ) RELEVANT RESIDUES IN SEQ ID NO:2: FROM 1 TO 426

( x ) PUBLICATION INFORMATION:
    ( H ) DOCUMENT NUMBER: CS PV2323-92
    ( I ) FILING DATE: 24-JUL-1992
    ( K ) RELEVANT RESIDUES IN SEQ ID NO:2: FROM 1 TO 426

( x ) PUBLICATION INFORMATION:
    ( H ) DOCUMENT NUMBER: HU P9202439
    ( I ) FILING DATE: 24-JUL-1992
    ( K ) RELEVANT RESIDUES IN SEQ ID NO:2: FROM 1 TO 426

( x i ) SEQUENCE DESCRIPTION: SEQ ID NO:2:

```
Met Asn Asp Ser Glu Leu His His Leu Glu Leu Leu Glu Val Gly Arg
 1               5                  10                  15

Glu Ile Gln Ser Arg Arg Ile Ser Ser Glu Glu Val Thr Arg His Met
             20                  25                  30

Leu Ala Arg Ile Glu Ala Val Asp Ala Arg Leu His Ser Tyr Val Thr
         35                  40                  45

Val Met Ala Gln Gln Ala Met Glu Asp Ala Arg Arg Ala Asp Ala Glu
     50                  55                  60

Ile Ala Gln Gly Ala Ala Ala Val Arg Cys Thr Ala Cys Arg Gly Ala
 65                  70                  75                  80

Gln Gly Pro Ala Val Asp Pro Gly Arg Pro His His Ala Trp Asn Asp
             85                  90                  95

Ala Ala Pro Arg Pro Ser Pro His Gly Arg Cys His Arg Gly Ala Gln
            100                 105                 110

Ala Ala Arg Gly Arg Arg Arg His Pro Gly Gln Ala Ala Ala Asp Arg
        115                 120                 125

Arg Arg Leu Arg Arg Pro Pro Ser Arg Asp His Cys Pro Arg Gln Pro
    130                 135                 140

Leu Glu Arg Pro Ala Met Ala Arg Gly Leu Val Gln Arg Leu Gly Arg
145                 150                 155                 160

Gly His Gly Gly Gly Ala Val Leu Arg Ile Ala Gly His Gly His Arg
                    165                 170                 175

Gly Leu His Pro Leu Ser Ile Gly Arg Gln Arg His His Gly Ala Gln
                180                 185                 190

Ala His Leu Gly Gln Gly Glu Pro Pro Arg Arg Leu Arg Thr Gly Arg
        195                 200                 205
```

| | | | | | | | | | | | | | | |
|---|---|---|---|---|---|---|---|---|---|---|---|---|---|---|
| Val | Pro | Gly | Pro | His | Arg | Pro | Asp | Gly | Ala | Gln | Cys | Cys | Arg | Cys | Arg |
| | 210 | | | | | 215 | | | | | 220 | | | | |
| Ser | His | Ala | Arg | Gly | His | Arg | Arg | Gly | Gly | Pro | Ala | Gly | Pro | Tyr | Gly |
| 225 | | | | | 230 | | | | | 235 | | | | | 240 |
| Gln | Pro | Val | Gln | Arg | Ala | Arg | Leu | Ser | Gly | His | Asp | Asp | Ala | Arg | Ile |
| | | | | 245 | | | | | 250 | | | | | 255 | |
| Leu | Arg | Pro | Ala | Pro | Gly | His | Gly | Pro | Ala | Met | Gly | Thr | Gly | Arg | Arg |
| | | | 260 | | | | | 265 | | | | | 270 | | |
| Gly | Cys | Pro | Leu | Pro | Pro | Gly | Gly | Gly | Ala | Gly | Pro | Gly | Gly | Gly | Ala |
| | | 275 | | | | | 280 | | | | | 285 | | | |
| Ala | Pro | Gly | Gly | Gln | Arg | Ala | Gly | Gly | Pro | Leu | Ser | Arg | Cys | His | Pro |
| | 290 | | | | | 295 | | | | | 300 | | | | |
| Gly | Gly | Gly | Gly | Leu | Ala | Gly | Ala | Val | Arg | Gly | Gly | Asp | Arg | Arg | Gly |
| 305 | | | | | 310 | | | | | 315 | | | | | 320 |
| Ala | Arg | Arg | His | Val | Pro | Cys | Thr | Ala | Arg | Gly | Leu | Trp | Pro | Arg | Ala |
| | | | | 325 | | | | | 330 | | | | | 335 | |
| Arg | Arg | Val | Asp | Arg | Pro | Gly | Ala | Gly | Pro | Val | Arg | His | Arg | Leu | Pro |
| | | | 340 | | | | | 345 | | | | | 350 | | |
| Ala | Ala | Ala | Ala | Ala | Pro | Arg | Gly | Leu | His | Gly | Pro | Gly | Ala | Cys | Thr |
| | | 355 | | | | | 360 | | | | | 365 | | | |
| Leu | Arg | Ala | Gly | Gly | Ser | Ala | Ala | Gly | Pro | Arg | His | Gly | Leu | Cys | Gly |
| | 370 | | | | | 375 | | | | | 380 | | | | |
| Pro | His | Ala | Ala | Thr | His | Gly | Ala | Phe | Arg | Leu | Arg | Cys | Arg | Ala | Val |
| 385 | | | | | 390 | | | | | 395 | | | | | 400 |
| Leu | Gly | His | Ala | Ala | Leu | His | Leu | Pro | Val | Arg | Pro | His | Gly | Gln | Pro |
| | | | | 405 | | | | | 410 | | | | | 415 | |
| His | Asp | His | Ala | Ala | Arg | Arg | Thr | His | Phe | | | | | | |
| | | | 420 | | | | | 425 | | | | | | | |